United States Patent [19] [11] 4,356,114
Kadowaki et al. [45] Oct. 26, 1982

[54] PROCESS FOR PRODUCING COMPOSITE OXIDE CATALYSTS

[75] Inventors: Koju Kadowaki; Kohei Sarumaru; Yoshiaki Tanaka, all of Ami, Japan

[73] Assignee: Mitsubishi Petrochemical Company Limited, Japan

[21] Appl. No.: 262,137

[22] Filed: May 11, 1981

[30] Foreign Application Priority Data

May 19, 1980 [JP] Japan .................................. 55/66295

[51] Int. Cl.³ ........................ B01J 23/20; B01J 23/22; B01J 23/28
[52] U.S. Cl. .................................... 252/467; 562/535
[58] Field of Search .......................... 252/467; 562/535

[56] References Cited

U.S. PATENT DOCUMENTS 3,557,199 1/1971 Parthasarathy et al. ....... 252/467 X
3,773,828 11/1973 Kadowaki et al. ............. 252/467 X
4,259,211 3/1981 Krabetz et al. ................. 252/467 X Primary Examiner—W. J. Shine
Attorney, Agent, or Firm—Robert E. Burns; Emmanuel J. Lobato; Bruce L. Adams

[57] ABSTRACT

In the production of a composite oxide catalyst containing at least Mo together with V and (or) Nb, the catalyst precursor is subjected to a thermal decomposition step in which: (1) the precursor is heated in a heat-exchanger type apparatus in which a first space accommodating the precursor and a second space through which a heating fluid flows are partitioned and separated from each other, the heating of the precursor being accomplished through the partitioning; (2) the thermal decomposition is carried out as an atmosphere gas of an oxygen concentration of 0.05 to 5 percent is caused to flow through the first space; and (3) the maximum temperature reached in the thermal decomposition is 300° to 550° C.

4 Claims, 8 Drawing Figures

PROCESS FOR PRODUCING COMPOSITE OXIDE CATALYSTS

BACKGROUND OF THE INVENTION

This invention relates generally to processes for producing catalysts comprising composite oxides. More specifically, the invention relates to a process for producing composite oxide catalysts which process, in the production of a composite oxide catalyst containing at least molybdenum together with vanadium and/or niobium by a method including thermal decomposition of the precursor compounds of the constituents, is characterized by the mode of carrying out the thermal decomposition. A catalyst thus produced in accordance with this invention is particularly suitable for use as a catalyst for gaseous-phase catalytic oxidation.

Oxidation catalysts comprising composite oxides containing molybdenum as well as vanadium and/or niobium are known. From the viewpoint of catalytic performance, these are catalysts for forming, for example, unsaturated carboxylic acid by catalytic oxidation of unsaturated aldehydes having 3 to 4 carbon atoms, that is, catalysts for producing acrylic acid from acrolein and methacrylic acid from methacrolein. Furthermore, catalysts having the capacity to oxidatively dehydrogenate saturated aldehydes or saturated carboxylic acid thereby to convert the same into unsaturated aldehydes or unsaturated carboxylic acid are also known.

Specific examples of known catalysts are as follows, the cited references being publications of the Japanese Patent Office. Catalysts which are for oxidation of acrolein to form acrylic acid and comprise molybdenum and vanadium are described in Pat. Publn. Nos. 12129/1969, 48371/1972, 19296/1973, and 169/1974 and Pat. Laid-Open Publn. Nos. 43922/1974 and 124016/1974. Those comprising molybdenum and niobium are disclosed in Pat. Publn. No. 37849/1978 and Pat. Laid-Open Publn. No. 29483/1977. Those comprising molybdenum, vanadium, and niobium are disclosed in Pat. Laid-Open Publn. Nos. 61117/1974, 93918/1975, and 23589/1977.

Catalysts which are for oxidation of methacrolein to form methacrylic acid and comprise molybdenum and vanadium are described in, for example, Pat. Laid-Open Publn. Nos. 57117/1977, 113818/1976, 122317/1977, 62220/1977, and 90214/1978. Those comprising molybdenum and niobium are described in, for example, Pat. Laid-Open Publn. No. 68122/1977. Those comprising molybdenum, vanadium, and niobium are disclosed in Pat. Laid-Open Publn. Nos. 90214/1978 and 36212/1979.

Examples of oxidative dehydrogenation catalysts are a catalyst for forming methacrylic acid by oxidatively dehydrogenating isobutyric acid as disclosed in Pat. Publn. No. 8654/1979 and a catalyst for forming methacrolein and methacrylic acid by oxidatively dehydrogenating isobutylaldehyde as disclosed in Pat. Laid-Open Publn. No. 124211/1978.

Thus, it is known that catalysts containing molybdenum together with vanadium and/or niobium are effective when used in oxidation or oxidative dehydrogenation reaction to form carboxylic acid. While a catalyst is not necessarily effective in a common manner with respect to all of the above enumerated reactions, a common feature of these catalysts is that each comprises, as constituent elements, molybdenum used as the principal ingredient and, further, vanadium and/or niobium added as essential ingredient(s).

A composite oxide catalyst of the above described character is produced by a process including a step in which thermally decomposable compounds which are starting materials for ordinarily providing constituent elements are thermally decomposed in an oxidizing atmosphere. Since this thermal decomposition step relates to the formation of catalyst ingredients by decomposing the precursor compounds of these catalyst ingredients, it can reasonably be considered to constitute a step in the catalyst production process. However, because the catalyst is formed in an activated state by undergoing this step, this step may be considered to be an activation step in some cases. Furthermore, since a temporary heating state continues even after the thermal decomposition, this step may be considered to be a heat treatment step in some cases. This thermal decomposition is called firing, baking, burning, or calcining in some instances.

This thermal decomposition step has heretofore been ordinarily carried out in a muffle furnace or a tunnel kiln, in which the atmosphere has ordinarily been air (that is, an oxygen concentration of 20 percent).

SUMMARY OF THE INVENTION

As a result of our research, we have discovered that the activity of a catalyst produced by a process as described above is greatly influenced by the production conditions, particularly the thermal decomposition conditions, even when the constituent ingredients of the catalyst are the same.

It is an object of this invention to obtain maximum catalyst activities on the basis of this discovery. This object has been achieved by adopting special conditions of thermal decomposition.

According to this invention, briefly summarized, there is provided a process for producing a composite oxide catalyst comprising at least molybdenum together with vanadium and/or niobium, which process includes a step of thermal decomposition of a catalyst precursor comprising a mixture of and/or a complex of compounds of the source of constituent elements in which process the thermal decomposition step is carried out under the conditions that:

(1) the catalyst precursor is heated in a vessel of a heat-exchanger structure wherein a first space accommodating the catalyst precursor and a second space through which a fluid for heating flows are partitioned from each other by a partitioning structure and thereby separated, and, moreover, heating of the catalyst precursor is accomplished through the partitioning structure;

(2) the thermal decomposition step is carried out as an atmosphere gas in which oxygen concentration has been adjusted to a value within a range of 0.05 to 5 percent is caused to flow through said first space; and (3) the maximum temperature reached in the thermal decomposition step is in a range of 300° to 550° C.

Thus, the thermal decomposition step according to this invention is characterized in that the catalyst precursor to be thermally decomposed is indirectly heated in an atmosphere of limited oxygen concentration, and in that this indirect heating is carried by means of a so-called heat-exchanger type apparatus under a limited temperature condition with the catalyst precursors and the heating medium in a state wherein they are in contact through side walls or tube walls of the heat exchanger.

Heretofore, it has not necessarily been clear that, in the case where a catalyst comprising composite oxides containing at least molybdenum together with vanadium and/or niobium is produced through a step of thermal decomposition of the catalyst precursor, the thermal decomposition conditions have a great influence on the activity of the catalyst obtained. In view of this, the discovery that a catalyst activity higher than that obtainable by a known process can be obtained by carrying out this thermal decomposition under specific and limited conditions is believed to be unexpected. Particularly, the elevation of the catalyst activity as a result of lowering the oxygen concentration in the thermal decomposition atmosphere in conjunction with the other conditions is very interesting.

The nature, utility, and further features of this invention will be more clearly apparent from the following detailed description beginning with a consideration of the general aspects of the invention and concluding with specific examples of practice thereof and comparison examples.

DETAILED DESCRIPTION OF THE INVENTION

1. Catalyst ingredients

Figure 1:
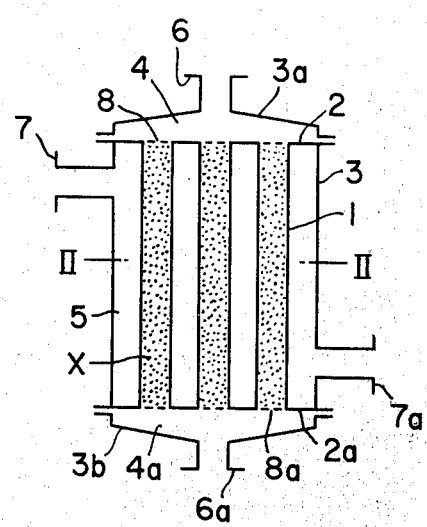
FIGS. 1, 3, 5 and 7 are elevations, in vertical section, respectively showing first through fourth examples of thermal decomposition apparatuses suitable for use in practicing this invention.

The composite oxide catalyst to be produced by the thermal decomposition step of this invention comprises, as its constitutent elements, at least molybdenum and vanadium, molybdenum and niobium, or molybdenum, vanadium, and niobium.

This catalyst may comprise only the above named essential constituent elements or it may contain, in addition, other ingredients. Examples of such other ingredients are tungsten, copper, germanium, uranium, manganese, nickel, iron, cobalt, tin, bismuth, antimony, zinc, cadmium, titanium, chromium, zirconium, rhodium, tantalum, indium, thallium, boron, phosphorus, alkali metals, and alkaline earth metals. Furthermore, this catalyst may contain a suitable support or carrier such as, for example, a refractory inorganic compound such as alumina, silica, silica-alumina, alundum, carborundum, or titania.

The kinds and proportions of these essential ingredients and optional ingredients are appropriately determined in accordance with the desired catalyst activity. Since this invention does not reside in the determination of specific proportions of the constituent ingredients of the catalyst, it should be sufficient to indicate proportions in parts of specific examples set forth hereinafter to be taken together with a number of known examples of catalysts of the instant kind enumerated hereinbefore.

2. Catalyst production—general description

The process of producing catalysts according to this invention does not differ, essentially, from the commonly practiced process except for the conditions of carrying out the thermal decomposition step.

Therefore, the following materials for producing catalysts are the most typical and may be used. As sources of molybdenum, ammonium molybdate, molybdic acid, molybdenum trioxide, etc., can be used. As sources of vanadium, ammonium vanadate, vanadium pentoxide, vanadyl oxalate, etc., can be used. As sources of niobium, niobium hydroxide, niobium oxalate, etc., can be used. Other than these compounds, salts of these metals of organic acids capable of being converted into oxides under the thermal decomposition conditions in the catalyst preparation process and other metal salts can also be used. In the case where the aforementioned other catalyst ingredients are added, starting materials of combination forms conforming to the above are selected. Depending on the necessity, as support or a carrier or as a dispersant of the catalyst ingredients, compounds such as silica, alumina, alundum, and carborundum can be used as stated hereinbefore.

These starting materials are mixed ordinarily in water (dissolved or suspended), and, when necessary, aqueous ammonia, an organic acid, or some other assistant is added. Then, as the materials are heated and agitated, aging is carried out thereby to form a catalyst precursor. The solution or slurry obtained is solidified by a suitable method such as evaporation to dryness, filtration of the precipitate, or spray drying in a stream of hot air. The resulting solid is subjected to thermal decomposition according to this invention, as described hereinafter in detail.

In general, it is necessary to form a catalyst into a suitable form or to cause it to be supported on a support depending on the manner in which it is to be used. Depending on this form, shaping is carried out in a suitable step in the above described process. For example, in the case where the catalyst is to be supported on a particulate support, the solution or slurry of the starting materials is poured into the support mass as it is rotated and is heated to evaporate off the water thereby to cause the catalyst to be supported. Another method comprises carrying out a heat treatment for the purpose of activation, pulverizing the solid thus obtained, adding water and kneading the mixture into a paste, and supporting the catalyst similarly as described above. In the case where forming is to be carried out by extruding, the procedure comprises pulverizing the solid prior to or after the thermal decomposition, suitably adjusting the moisture content by adding water and kneading, and extruding the material thus obtained to form the catalyst. In the case of tableting, the solid is pulverized into suitable particle size and tableted. The tableting step may be carried out prior to or after the thermal decomposition step.

3. Catalyst preparation—thermal decomposition

A first characteristic of this invention resides in the conditions of the thermal decomposition step in the catalyst preparation process as described above. The selection of these thermal decomposition conditions is vital, and, depending on its appropriateness or inappropriateness, the catalyst activity and selectivity vary greatly.

3-1. Thermal decomposition temperature

Firstly, the thermal decomposition temperature is in a range of 300° to 550° C., preferably 350° to 450° C. The optimum temperature differs somewhat with the catalyst composition. While a portion of the thermal decomposition in actual practice takes place also at temperatures below these in some cases, the effectiveness of this invention can be obtained by heating at a temperature within the above specified range.

3-2. Thermal atmosphere

The atmosphere contacted by the catalyst during the thermal decomposition is so controlled that the oxygen concentration therein will be 0.05 to 5 percent, preferably 0.1 to 3 percent. The constituents of this atmosphere other than oxygen are nitrogen, steam, carbon dioxide, and inactive gases such as helium. Depending on the catalyst composition, the coexistence particularly of steam results in some cases in an intensification of the activity of the catalyst formed. For this reason, it is recommended that the effectiveness of steam be tested beforehand. A simple measure for lowering the oxygen concentration is to dilute air with nitrogen gas, steam, or some other gas.

An atmosphere of low oxygen concentration of this character may be in a static state since the composition of the region of the catalyst in the vicinity of its outer surface is desirably maintained. However, as the temperature of the catalyst precursors is raised, the water content contained by the precursor itself or gases generated by the decomposition of the starting-material salts are given off, and, in order to remove this water or gases and obtain a controlled atmosphere, it is preferable to cause the atmosphere to flow toward the thermal decomposition zone. It is simple and convenient to carry out the thermal decomposition in an atmosphere gas under atmospheric pressure, but the decomposition can be carried out at a pressure somewhat above or below atmospheric pressure.

3-3. Thermal decomposition apparatus

A second characteristic of this invention resides in the construction of a vessel constituting the principal part of an apparatus used in the thermal decomposition in catalyst production on an industrial scale while satisfying the above described conditions. In the case where generally-used starting materials are used in the preparation of a catalyst, some reactions such as dehydration or decomposition of the salts or variations in the state of chemical or physico-chemical bonding in the solid phase or the like take place in the heating step and are accompanied by heat absorption and heat generation.

On the other hand, for obtaining catalysts in forms wherein they have maximum activities, the catalyst have respective optimum temperatures of thermal decomposition or heat treatment. For this reason, in order to cause all of the catalyst precursors to have uniformly a common optimum temperature, it is necessary to rapidly impart or remove the heat of heat absorption and/or heat generation. Accordingly, the vessel construction and method of heating in the apparatus becomes very important.

It is contemplated in this invention to achieve this object through the use of a vessel of heat-exchanger type. The shape and other physical features of this vessel are not particularly limited provided that it has a constructional organization such that the catalyst and a heating medium for heating are essentially separated by a partitioning structure, through which heat is transferred, and that the catalyst precursor is accommodated in chambers having sides along which an atmosphere gas of controlled oxygen concentration can flow and pass by.

Such a vessel of heat-exchanger type, in general, has a structural organization in which a plurality of small chambers in mutually-communicative parallel arrangement are accommodated within a housing, and one of the two kinds of mediums to participate in the heat exchange is placed in these small chambers while the other medium is caused to flow through the housing interior thereby to cause indirect heat exchange between the two kinds of mediums. One specific example of the plurality of small chambers in this case is a bundle of a plurality of tubes. Accordingly, one specific example of a heat-exchanger type vessel of this character is a vessel of the so-called shell-and-tube heat-exchanger type in which a tube bundle of this character is accommodated within a housing or shell.

The catalyst precursors to be processed according to this invention are accommodated within the small chambers of such a heat-exchanger type vessel, and a fluid for heating is caused to flow through the interior of the housing outside of the small chamber. The reverse state of these mediums is also possible. The heat-decomposition atmosphere gas of low oxygen content is caused to flow through from a suitable manifold into and through all of the small chambers in parallel communication thereby to maintain the thermal decomposition region within the small chambers at a specific oxygen concentration.

The fluid for heating may be a gas, or it may be a liquid. Compositionally, it may be the same as the thermal decomposition atmosphere gas, in which case it is possible to cause the space for accommodating the catalyst precursor and the space for accommodating the fluid for heating to be communicative and to supply heated low-oxygen gas to only the latter space thereby to realize the required thermal decomposition conditions.

3-4. Carrying out the thermal decomposition

The thermal decomposition is advantageously carried out under the conditions of the above stated temperature range and oxygen concentration range and by the specific indirect heating method as described above. It is not necessary to fix the temperature range and the oxygen concentration range at respective constant values throughout the thermal decomposition step. For example, with respect to the oxygen concentration, even when the oxygen concentration within the supplied gas is caused to be constant, gases due to decomposition are given off as the thermal decomposition progresses, whereby the oxygen concentration in the thermal decomposition atmosphere is temporarily lowered in some cases. Under such circumstances, also, it is desirable to set the flow velocity of the atmosphere gas so that its oxygen concentration will be held within the specified range.

While the rate of temperature rise until the prescribed thermal decomposition temperature is reached is optional, it is ordinarily within the range of 10° to 400° C. per hour. Depending on the catalyst composition, a heating range which is slightly on the lower side produces a desirable result in some cases. The heating time period after the prescribed temperature has been reached is at least a period sufficient for completion of the thermal decomposition, but it is also possible to continue the heating after completion of the thermal decomposition in order to carry out heat treatment of the catalyst formed. In general, the heating time period after the prescribed thermal decomposition temperature has been reached is ordinarily of the order of 0.5 to 10 hours, preferably of the order of 1 to 6 hours.

It is preferable to cause the thermal decomposition atmosphere gas to flow through the thermal decomposition region. The flow rate in this case is determined by the mutual relationship with the gases generated in the thermal decomposition, but, in general, it is ordinarily of the order of 5 to 500 times the volumetric flow rate of the materials undergoing thermal decomposition per hour. In the case where the thermal decomposition atmosphere gas is caused to flow through the thermal decomposition region, it is desirable that this gas be in a suitably heated state so as not to disturb the above described thermal decomposition temperature condition or so as to contribute to the maintenance thereof. Furthermore, it is preferable that the thermal decomposition atmosphere gas be caused to flow through the thermal decomposition region also during the displacement period until the temperature of the catalyst precursors reaches the prescribed thermal decomposition temperature.

The catalyst precursor is heated indirectly through a certain heat-transfer area, but the heat-transfer area with respect to the material to undergo thermal decomposition should be determined with consideration of factors such as the quantities of the absorbed heat and generated heat and the allowable range of temperature. A suitable heat-transfer area per unit volume of the catalyst precursor is, for example, of the order of 20 to 200 $m^2/m^3$.

4. Specific examples of thermal decomposition apparatus

Specific examples in concrete form of thermal decomposition apparatuses suitable for use in the practice of this invention will now be described in conjunction with FIGS. 1 through 8 of the accompanying drawings. Each of these apparatuses may be one which is used only for carrying out the thermal decomposition process of this invention, but it may also be one which is so designed and fabricated that, without the catalyst formed therewithin being taken out thereof, the catalyst can be used directly as it is to carry out an oxidation reaction in the same apparatus.

Figure 2:
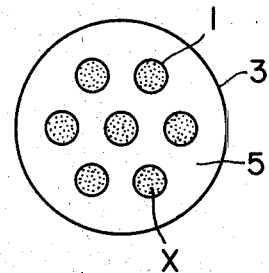
FIGS. 2 and 4 are sections respectively along the planes indicated by lines II—II and IV—IV in FIGS. 1 and 3, respectively.

The first example illustrated in FIGS. 1 and 2 is an apparatus of shell-and-tube heat-exchanger type in which the small chambers for accommodating the catalyst precursor comprise the interiors of a plurality of tubes. In this apparatus, since the catalyst precursor and the fluid for heating are completely separated from each other, and, furthermore, the heat-transfer area can be made amply large, strict control of the process conditions is possible.

In this apparatus shown in FIGS. 1 and 2, a plurality of tubes 1 in which catalyst precursor X is accommodated in portions are fixedly supported in the form of a tube bundle by tube sheets 2 and 2a, which in turn are supported by and in a housing or shell 3. The bundle of tubes 1 and the tube sheets 2 and 2a are thus enclosed within the shell 3. The shell 3 is provided at its ends with shell covers 3a and 3b, respectively, between which and the tube sheets 2 and 2a, manifold chambers 4 and 4a are formed. The tubes 1 are all made mutually communicative at their ends by these manifold chambers 4 and 4a.

A space 5, which is separated from the interiors of the tubes 1 by the walls of these tubes, is formed between and by the cylindrical wall of the shell 3 and the tube sheets 2 and 2a. Communicating with this space 5 are an inlet 7a and an outlet 7 for the fluid for heating, which are provided in the wall of the shell 3 near opposite ends thereof. The shell covers 3a and 3b are respectively provided with an outlet 6 and an inlet 6a for thermal decomposition atmosphere gas, which communicate with the manifold chambers 4 and 4a, respectively. The above mentioned catalyst precursors X are retained within the tubes 1 by perforated plates 8 and 8a disposed at the ends of the tubes.

In carrying out the thermal decomposition step by the use of this apparatus, firstly, a fluid for heating at a suitable temperature is caused to flow through the fluid inlet 7a into the space 5 and to flow out therefrom through the outlet 7. The fluid for heating thus discharged is ordinarily reheated and recycled. Then a thermal decomposition atmosphere gas of adjusted oxygen concentration is introduced through the inlet 6a into the manifold chamber 4a and caused to flow through the tubes 1 into the manifold chamber 4 and to be discharged through the outlet 6a. This gas is thereby caused to form a thermal decomposition atmosphere around the precursor X in the tubes 1.

The charging of the catalyst precursor into the tubes 1 and the taking out of the thermally decomposed material therefrom is carried out by detaching a shell cover 3a or 3b and the perforated plates 8 or 8a.

Figure 3:
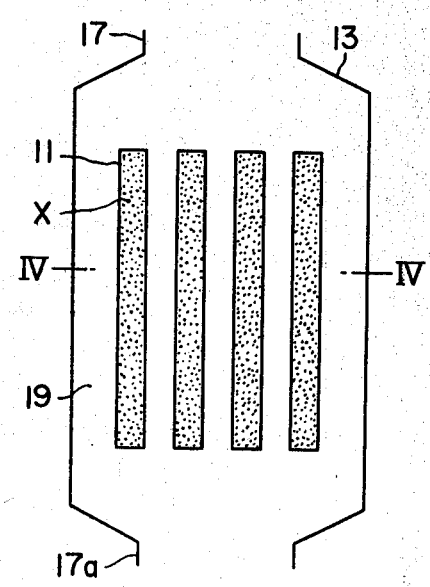
Figure 4:
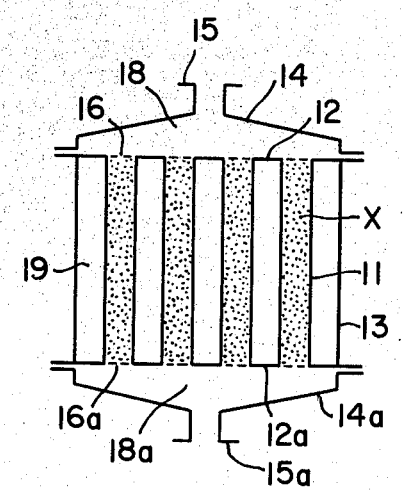

In the second example shown in FIGS. 3 and 4 of the thermal decomposition apparatus, the small chambers for accommodating the catalyst precursor X are formed by the walls of a plurality of box-shaped structures 11 each of relatively small dimension in the thickness direction. These structures 11 are fixedly supported in parallel spaced-apart arrangement by plates 12 and 12a corresponding to the tube sheets 2 and 2a in the preceding example and, together with the structures 11, are supported and enclosed within a housing 13. This housing 13 has a substantially square cross section, as shown in FIG. 4, and is provided with housing covers 14 and 14a, between which and the plates 12 and 12a, manifold chambers 18 and 18a are formed.

The housing covers 14 and 14a are respectively provided with an inlet 15 and an outlet 15a for thermal decomposition atmosphere gas communicating respectively with the manifold chambers 18 and 18a. The inlet 15 and outlet 15a can each be provided in plural number in directions perpendicular to the plane of FIG. 4. The catalyst precursor X is retained within the box-like structures 11 by perforated plates 16 and 16a.

The thermal decomposition atmosphere gas is introduced through the inlet 15 into the parts of the apparatus in contact with or associated with the process materials and discharged through the outlet 15a. On the other hand, the fluid for heating is introduced through an inlet 17 provided on one end of the housing 13 into a space 19 within the housing 13 outside of the box-like structures 11 and is discharged through an outlet 17a provided at the opposite end of the housing 13. Thus, the directions of flow of the two fluids are perpendicular to each other.

The charging of the catalyst precursors into the box-like structures 11 and the taking out therefrom of the thermally decomposed material is carried out by detaching the housing cover 14 or 14a and the perforated plates 16 and 16a.

Figure 5:
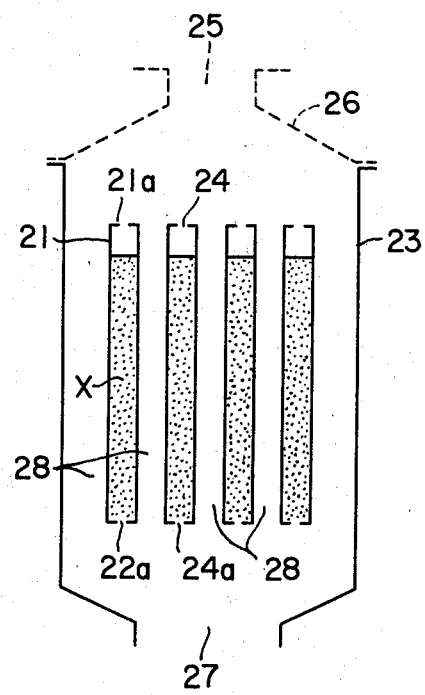
Figure 6:
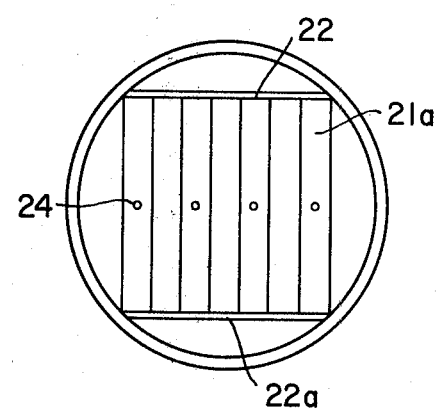
FIGS. 6 and 8 are plan views, as viewed from above, of the apparatuses shown in FIGS. 5 and 7, respectively.

The third example illustrated in FIGS. 5 and 6 is an example of the apparatus in the case where the thermal decomposition atmosphere gas is the same as the fluid for heating. The catalyst precursor X is accommodated within a plurality of box-shaped structures 21 forming small chambers therewithin and fixedly supported by and between plates 22 and 22a lying in planes parallel to the plane of FIG. 5. The plates 22 and 22a in turn are fixedly supported by and within a cylindrical housing 23.

Each of the box-shaped structures 21 is provided at each of its upper part 21a and lower part 22a with one or more gas inlets or outlets or orifices 24 and 24a. As indicated by dotted lines in FIG. 5, the housing 23 is provided at its top with a housing cover 26 having a gas inlet 25.

When a gas which can be used as the thermal decomposition atmosphere gas and as the fluid for heating is introduced through the gas inlet 25 into the interior of the housing 23, the greater portion of this gas flows through the space 28 between and around the box-shaped structures 21 and, as it thus flows, imparts heat necessary for the thermal decomposition reaction occurring within the structures 21, finally leaving the interior of the housing 23 through a gas outlet 27. On the other hand, the remainder of the gas entering through the inlet 25 flows into the interiors of the box-shaped structures 21 through the orifices 24 provided at their upper parts and, after flowing through the structures 21 to create the prescribed condition of oxygen concentration in the thermal decomposition region, flows out through the lower orifices 24a and thence through the outlet 27.

Figure 7:
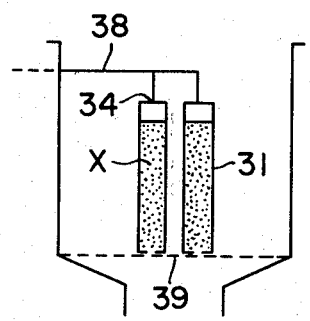
Figure 8:
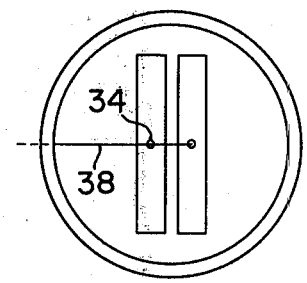

FIGS. 7 and 8 illustrate the fourth specific example of the apparatus, which is similar to the third example shown in FIGS. 5 and 6 except that the thermal decomposition atmosphere gas is supplied separately from the fluid for heating. This fourth specific example differs from the preceding example in that the thermal decomposition atmosphere gas is supplied through piping 38 to an orifice 34 provided at the top of each box-shaped structure 31 for holding the catalyst precursor X. Another difference is that all of the box-shaped structures 31 are placed in spaced-apart positions on a horizontal perforated plate 39. In other essential features, this fourth example is similar to the preceding third example.

5. Examples of practice

In order to indicate more fully the nature and utility of this invention the following specific examples of practice thereof and comparison examples are set forth, it being understood that these examples are presented as illustrative only and are not intended to limit the scope of the invention.

EXAMPLES 1, 2, AND 3, COMPARISON EXAMPLES 1, 2, AND 3

By the process disclosed in Example 1 of Japanese Pat. Laid-Open Publn. No. 23589/1977, the production of a catalyst of the following composition was carried out up to and including the step before calcination

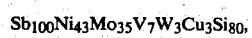

$Sb_{100}Ni_{43}Mo_{35}V_7W_3Cu_3Si_{80}$, wherein the compositional proportions are indicated as an atomic ratio, and oxygen is omitted.

As a single-tube heat exchanger, a reaction tube with a stainless-steel jacket for nitrate heating medium of 20-mm inner diameter and 500-mm length was used. In each example, this reaction tube was charged with 50 ml of the above described uncalcined catalyst. Then, as the respective gas mixture of the composition shown in Table 1 was caused to flow through the reaction tube at a flow rate of 10 liters/hour (based on 0° C./one atmospheric pressure), the reaction system was heated at a rate of temperature rise of approximately 130° C./hour to 390° C., at which the reaction system was held for 3 hours thereby to produce a catalyst.

In Comparison Example 3, the uncalcined catalyst was placed in a muffle furnace which had been preheated to 390° C., and the catalyst was taken out of the kiln after the elapse of 5 hours.

By directly using the same apparatus in which the catalyst thus formed was accommodated, in each example, catalytic oxidation of acrolein was carried out. For the starting-material gas, a gas mixture of 4 percent of acrolein, 46 percent of steam, and 50 percent of air was caused to flow through the reaction tube at a space velocity of 750 h$^{-1}$ (based on 0° C.). The results of the reactions are set forth in Table 2. Principal products formed other than those shown were acetic acid, acetoaldehyde, carbon dioxide, and carbon monoxide.

TABLE 1

| Example | Atmosphere gas composition (%) | | | (Process temp.) × (Time) | |
|---|---|---|---|---|---|
| | Oxygen | Steam | Nitrogen | (°C.) | (h) |
| Example 1 | 0.2 | — | 99.8 | 390 × | 3 |
| Example 2 | 0.4 | — | 99.6 | 390 × | 3 |
| Example 3 | 1 | 10 | 89 | 390 × | 3 |
| Comparison Example 1 | — | — | 100 | 390 × | 3 |
| Comparison Example 2 | 21 | — | 79 | 390 × | 3 |
| Comparison Example 3 | (Static air ... muffle furnace) | | | 390 × | 5 |

TABLE 2

| Example | Reaction temp. (°C.) | Acrolein conversion (%) | Acrylic acid yield (%) | Acrylic acid selectivity (%) |
|---|---|---|---|---|
| Example 1 | 250 | 99.0 | 94.3 | 95.3 |
| Example 2 | 250 | 99.2 | 94.8 | 95.6 |
| Example 3 | 250 | 98.8 | 93.8 | 94.9 |
| Comparison Example 1 | 270 | 98.2 | 87.6 | 89.2 |
| Comparison Example 2 | 270 | 93.5 | 82.9 | 88.7 |
| Comparison Example 3 | 270 | 98.4 | 90.7 | 92.2 |

EXAMPLE 4, COMPARISON EXAMPLES 4 AND 5

By the process disclosed in Example 5 of Japanese Pat. Laid-Open Publn. No. 23589/1977, the production of a catalyst of the following composition was carried out up to and including the step before calcination.

$Sb_{100}Ni_{43}Mo_{35}V_7Nb_3Cu_3Si_{80}$

This uncalcined catalyst was subjected to a thermal decomposition or calcination process by the procedure specified in Example 1 in the gas atmospheres of the compositions set forth in Table 3 thereby to produce a catalyst. Under the conditions of Example 1 except the reaction temperature, oxidation of acrolein was carried out, whereupon the results shown in Table 4 were obtained.

TABLE 3

| Example | Atmosphere gas composition (%) | | | (Process temp.) × (Time) | |
|---|---|---|---|---|---|
| | Oxygen | Steam | Nitrogen | (°C.) | (h) |
| Example 4 | 0.5 | 7.5 | 92 | 380 × | 3 |
| Comparison Example 4 | 21 | — | 79 | 380 × | 3 |
| Comparison Example 5 | 10.5 | — | 89.5 | 380 × | 3 |

TABLE 4

| Example | Reaction temp. (°C.) | Acrolein conversion (%) | Acrylic acid yield (%) | Acrylic acid selectivity (%) |
|---|---|---|---|---|
| Example 4 | 250 | 99.4 | 95.0 | 95.6 |
| Comparison Example 4 | 270 | 93.5 | 82.9 | 88.7 |
| Comparison Example 5 | 270 | 98.2 | 87.5 | 89.1 |

EXAMPLES 5 AND 6, COMPARISON EXAMPLE 6

A catalyst was prepared as described below according to the process disclosed in Example 8 of Japanese Pat. Publn. No. 169/1974.

5.0 grams (g) of vanadium pentoxide was suspended in 300 ml of pure water, and, as the resulting suspension was heated, 10 g of oxalic acid was added thereto and dissolved therein. To this solution was added a solution prepared by dissolving 47.6 g of ammonium paramolybdate in 200 ml of pure water under heating. To the resulting solution, 3.5 g of ferrous chloride and 5.3 g of bismuth nitrate were gradually added, and the materials were mixed. Silicasol containing 10 g of $SiO_2$ was added to an mixed with the resulting mixture. To the resulting mixture, 200 g of porous carborundum in the form of spheres each of 3-mm diameter was added as a carrier, and, as the mixture was agitated over a hot-water bath, it was evaporated to dryness thereby to cause the catalyst ingredients to adhere to the carrier.

The uncalcined catalyst thus obtained was subjected to thermal decomposition by the process specified in Example 1 under the conditions set forth in Table 5 thereby to obtain a catalyst. The concentration of the catalyst calculated from the increase in weight of this catalyst after thermal decomposition was 16.7 percent. The composition of the catalyst carried calculated from the quantity of the charged starting materials was as follows.

$Mo_{100}V_{20}Fe_{10}Bi_4Si_{60}$

These catalysts were used for oxidizing acrolein under the conditions of Example 1 except for the reaction temperature, whereupon the results shown in Table 6 were obtained.

TABLE 5

| Example | Atmosphere gas composition (%) | | | (Process temp.) × (Time) | |
|---|---|---|---|---|---|
| | Oxygen | Steam | Nitrogen | (°C.) | (h) |
| Example 5 | 0.4 | — | 99.6 | 380 × | 3 |
| Example 6 | 1 | 10 | 89 | 380 × | 3 |
| Comparison Example 6 | 21 | — | 79 | 380 × | 3 |

TABLE 6

| Example | Reaction temp. (°C.) | Acrolein conversion (%) | Acrylic acid yield (%) | Acrylic acid selectivity (%) |
|---|---|---|---|---|
| Example 5 | 260 | 99.3 | 93.4 | 94.1 |
| Example 6 | 260 | 99.1 | 93.1 | 93.9 |
| Comparison Example 6 | 280 | 97.5 | 89.7 | 92.0 |

EXAMPLE 7, COMPARISON EXAMPLES 7 AND 8

A catalyst of the following composition was prepared by the process disclosed in Example 1 of Japanese Pat. Laid-Open Publn. No. 29483/1977.

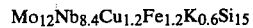
$Mo_{12}Nb_{8.4}Cu_{1.2}Fe_{1.2}K_{0.6}Si_{15}$

The uncalcined catalyst was subjected to thermal decomposition under the conditions shown in Table 7 thereby to produce a catalyst. In Comparison Example 8, the uncalcined catalyst was placed in a preheated muffle furnace and processed for 5 hours. With the use of these catalysts, oxidation of acrolein was carried out similarly as in Example 1. The results are shown in Table 8.

TABLE 7

| Example | Atmosphere gas composition (%) | | | (Process temp.) × (Time) | |
|---|---|---|---|---|---|
| | Oxygen | Steam | Nitrogen | (°C.) | (h) |
| Example 7 | 0.4 | — | 99.6 | 420 × | 3 |
| Comparison Example 7 | 21 | — | 89 | 420 × | 3 |
| Comparison Example 8 | (Static air ... muffle furnace) | | | 420 × | 5 |

TABLE 8

| Example | Reaction temp. (°C.) | Acrolein conversion (%) | Acrylic acid yield (%) | Acrylic acid selectivity (%) |
|---|---|---|---|---|
| Example 7 | 240 | 98.3 | 93.9 | 95.5 |
| Comparison Example 7 | 260 | 95.1 | 84.9 | 89.3 |
| Comparison Example 8 | 250 | 97.2 | 90.5 | 93.1 |

EXAMPLE 8

A heat-exchanger type baking apparatus comprising a vertical cylindrical furnace heated by combustion gas flowing therethrough and two flat box-shaped containers each of 50-mm width, 300-mm length, and 250-mm height, functioning as catalyst precursor containers and disposed with a 20-mm spacing therebetween in the furnace as shown in FIGS. 7 and 8 was used.

A nozzle was provided at the center of the upper part of each of the above described containers and connected to stainless-steel pipe through which an air-nitrogen mixture could be supplied. Each container was provided at its bottom with an exhaust gas outlet. Each container was filled with 3.5 liters of an uncalcined catalyst of the same composition as that in Example 1 and installed within the furnace. Then, as a gas mixture comprising 2 percent of air and 98 percent of nitrogen was caused to flow at a total flow rate of 500 liters/hour through the two containers, combustion gas (exhaust combustion gas of city gas) was caused to flow through the furnace from the top to the bottom thereby to raise the temperature of its interior to 380° C. in 3 hours. This temperature was maintained for a further 3 hours thereby to carry out thermal decomposition.

From the catalyst thus produced, 50 ml was taken and used in an acrolein oxidation reaction under the same reaction conditions as in Example 1. With a reaction temperature of 240° C., the acrolein conversion was 99.5 percent; the acrylic acid yield was 94.3 percent; and the acrylic acid selectivity was 94.8 percent.

What is claimed is:

1. In a process for producing a composite oxide catalyst comprising at least molybdenum together with vanadium and/or niobium, which process includes a step of thermal decomposition of a catalyst precursor comprising a mixture of compounds and/or a complex compound of the source of constituent elements, the improvement in which the thermal decomposition step is carried out under the conditions that:

(1) the catalyst precursor is heated in a vessel of a heat-exchanger structure wherein a first space accommodating the catalyst precursor and a second space through which a fluid for heating flows are partitioned from each other by a partitioning structure and thereby separated, and, moreover, heating of the catalyst precursor is accomplished through the partitioning structure;

(2) the thermal decomposition step is carried out as an atmosphere gas in which oxygen concentration has been adjusted to a value within a range of 0.05 to 5 percent is caused to flow through said first space; and (3) the maximum temperature reached in the thermal decomposition step is in a range of 300° to 550° C.

2. A process according to claim 1 in which said reaction vessel is of a construction which is essentially that of a shell-and-tube heat exchanger comprising a shell and a bundle of a plurality of tubes disposed within the shell, said first space being the interiors of the tubes and said second space being the interior space within the shell and outside of the tubes.

3. A process according to claim 1 in which said reaction vessel comprises a shell structure and a plurality of containers, each of relatively small dimension in a thickness direction thereof, disposed in spaced-apart arrangement within the shell structure, said first space being the interiors of the containers and said second space being the interior space within the shell structure and outside of the containers.

4. A process according to claim 1 in which the fluid for heating and the atmosphere gas are the same gas.

* * * * *